US007388138B1

(12) United States Patent
Miller

(10) Patent No.: US 7,388,138 B1
(45) Date of Patent: Jun. 17, 2008

(54) INBRED CORN LINE G06-NP2608

(75) Inventor: Bob Miller, Iowa City, IA (US)

(73) Assignee: Syngenta Participations AG, Basel (CH)

( * ) Notice: Subject to any disclaimer, the term of this patent is extended or adjusted under 35 U.S.C. 154(b) by 31 days.

(21) Appl. No.: 11/364,582

(22) Filed: Feb. 28, 2006

(51) Int. Cl.
*A01H 1/00* (2006.01)
*A01H 1/02* (2006.01)
*A01H 5/10* (2006.01)
*A01H 5/00* (2006.01)
*C12N 5/04* (2006.01)

(52) U.S. Cl. .................... 800/320.1; 800/260; 800/275; 800/278; 800/279; 800/295; 800/298; 800/300.1; 800/302; 800/303; 435/412; 435/424; 435/468; 435/430.1

(58) Field of Classification Search ................ 800/320.1
See application file for complete search history.

(56) References Cited

U.S. PATENT DOCUMENTS

| 5,134,074 A | 7/1992 | Gordon et al. |
| 5,177,010 A | 1/1993 | Goldman |
| 5,302,523 A | 4/1994 | Coffee |
| 5,464,765 A | 11/1995 | Coffee |
| 5,484,956 A | 1/1996 | Lundquist |
| 5,489,520 A | 2/1996 | Adams |
| 5,596,838 A | 1/1997 | Greaves |
| 6,706,955 B2 | 3/2004 | Miller |
| 7,135,629 B2 * | 11/2006 | Maves ..................... 800/320.1 |

OTHER PUBLICATIONS

PVP 8200064 issued May 26, 1983.
PVP 8300148 issued Feb. 22, 1985.

* cited by examiner

*Primary Examiner*—Medina A. Ibrahim
(74) *Attorney, Agent, or Firm*—Dana Rewoldt

(57) ABSTRACT

Basically, this invention provides for an inbred corn line designated G06-NP2608, methods for producing a corn plant by crossing plants of the inbred line G06-NP2608 with plants of another corn plants. The invention relates to the various parts of inbred G06-NP2608 including culturable cells. This invention also relates to methods for introducing transgenic transgenes into inbred corn line G06-NP2608 and plants produced by said methods.

31 Claims, No Drawings

US 7,388,138 B1

INBRED CORN LINE G06-NP2608

FIELD OF THE INVENTION

This invention is in the field of corn breeding, specifically relating to an inbred corn line designated G06-NP2608. This invention also is in the field of hybrid maize production employing the present inbred.

BACKGROUND OF THE INVENTION

The original maize plant was indigenous to the Western Hemisphere. The plants were weedlike and only through the efforts of early breeders were cultivated crop species developed. The crop cultivated by early breeders, like the crop today, could be wind pollinated. The physical traits of maize are such that wind pollination results in self-pollination or cross-pollination between plants. Each maize plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to, at most, incremental increases in seed yield.

Large increases in seed yield were due to the work done by land grant colleges that resulted in the development of numerous hybrid corn varieties in planned breeding programs. Hybrids were developed from inbreds which were developed by selecting corn lines and selfing these lines for several generations to develop homozygous pure inbred lines. One selected inbred line was emasculated and another selected inbred line pollinated the emasculated inbred to produce hybrid seed F1 on the emasculated inbred line. Emasculation of the inbred usually is done by detasseling the seed parent; however, emasculation can be done in a number of ways. For example an inbred could have a male sterility factor which would eliminate the need to detassel the inbred.

In the early seventies the hybrid corn industry attempted to introduce CMS (cytoplasmic male sterility) into a number of inbred lines. Unfortunately, the CMS inbreds also introduced some very poor agronomic performance traits into the hybrid seed which caused farmers concern causing the maize industry to shy away from CMS material for a couple of decades thereafter.

However, in the last 10-15 years a number of different male sterility systems for maize have been successfully deployed. The most traditionally of these male sterility and/or CMS systems for maize parallel the CMS type systems that have been routinely used in hybrid production in sunflower.

In the standard CMS system there are three different maize lines required to make the hybrid. First, there is a cytoplasmic male-sterile line usually carrying the CMS or some other form of male sterility. This line will be the seed producing parent line. Second, there must be a fertile inbred line that is the same or isogenic with the seed producing inbred parent but lacking the trait of male sterility. This is a maintainer line needed to make new inbred seed of the seed producing male sterile parent. Third there is a different inbred which is fertile, has normal cytoplasm and carries a fertility restoring gene. This line is called the restorer line in the CMS system. The CMS cytoplasm is inherited from the maternal parent (or the seed producing plant), therefore for the hybrid seed produced on such plant to be fertile the pollen used to fertilize this plant must carry the restorer gene. The positive aspect of this is that it allows hybrid seed to be produced without the need for detasseling the seed parent. However, this system does require breeding of all three types of lines: 1) male sterile—to carry the CMS: 2) the maintainer line; and, 3) the line carrying the fertility restorer gene.

In some instances, sterile hybrids are produced and the pollen necessary for the formation of grain on these hybrids is supplied by interplanting of fertile inbreds in the field with the sterile hybrids.

Whether the seed producing plant is emasculated by detasseling or by CMS or by transgenes, the seed produced by crossing two inbreds in this manner is hybrid seed. This hybrid seed is F1 hybrid seed. The grain produced by a plant grown from a F1 hybrid seed is referred to as F2 or grain. Although, all F1 seed and plants, produced by this hybrid seed production system using the same two inbreds should be substantially the same, all F2 grain produced from the F1 plant will be segregating maize material.

The hybrid seed production produces hybrid seed which is heterozygous. The heterozygosis results in hybrid plants, which are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogenity of the inbred maize lines is that all hybrid seed produced from any cross of two such elite lines will be the same hybrid seed and make the same hybrid plant. Thus the use of inbreds makes hybrid seed which can be reproduced readily.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soil. Thus, a variety of major agronomic traits is important in hybrid combination for the various Corn Belt regions, and has an impact on hybrid performance.

Inbred line development and hybrid testing have been emphasized in the past half-century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, Hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (corn Lethal necrosis and in the west soil that has excessively high pH levels. The industry often targets inbreds that address these issues specifically forming niche products. However, the aim of most large seed producers is to provide a number of traits to each inbred so that the corresponding hybrid can useful in a broader regions of the Corn Belt. The new biotechnology techniques such as Microsatellites, RFLPs, RAPDs and the like have provided breeders with additional tools to accomplish these goals.

SUMMARY OF THE INVENTION

The present invention relates to an inbred corn line G06-NP2608. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G06-NP2608.

Generally then, broadly the present invention includes an inbred corn seed designated G06-NP2608. This seed produces a corn plant.

The invention also includes the tissue culture of regenerable cells of G06-NP2608 wherein the cells of the tissue culture regenerates plants capable of expressing the genotype of G06-NP2608. The tissue culture is selected from the group consisting of leaf, pollen, embryo, root, root tip, guard cell, ovule, seed, anther, silk, flower, kernel, ear, cob, husk and stalk, cell and protoplast thereof. The corn plant regenerated from G06-NP2608 or any part thereof is included in the present invention. The present invention includes regenerated corn plants that are capable of expressing G06-NP2608's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G06-NP2608 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G06-NP2608 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G06-NP2608; cultivating corn plants resulting from said planting; permitting pollen from another inbred line to cross pollinate inbred line G06-NP2608; harvesting seeds produced on plants of the inbred; and growing a harvested seed are part of the method of this invention.

The present invention also encompasses a method of introducing at least one targeted trait into maize inbred line comprising the steps of: (A) crossing plant grown from the present invention seed which is the recurrent parent, representative seed of which has been deposited, with the donor plant of another maize line that comprises at least one target trait selected from the group consisting of male sterility, herbicide resistance, insect resistance, disease resistance, amylose starch, and waxy starch to produce F1 plants; (b) selecting from the F1 plants that have at least one of the targeted trait, forming a pool of progeny plants with the targeted trait; (c) crossing the pool of progeny plants with the present invention which is the recurrent parent to produce backcrossed progeny plants with the targeted trait; (d) selecting for backcrossed progeny plants that have at least one of the target trait and physiological and morphological characteristics of maize inbred line of the recurrent parent, listed in Table 1 forming a pool of selected backcrossed progeny plants; and (e) crossing the selected backcrossed progeny plants to the recurrent parent and selecting from the resulting plants for the targeted trait and physiological and morphological characteristics of maize inbred line of the recurrent parent, listed in Table 1 and reselecting from the pool of resulting plants and repeating the crossing to the recurrent parent and selecting step in succession to form a plant that comprise the desired trait and all of the physiological and morphological characteristics of maize inbred line of the recurrent parent if the present invention listed in Table 1 as determined at the 5% significance level when grown in the same environmental conditions.

This method and the following method of introducing traits can be done with less back crossing events if the trait and/or the genotype of the present invention are selected for or identified through the use of markers. SSR, microsatellites, SNP and the like decrease the amount of breeding time required to locate a line with the desired trait or traits and the characteristics of the present invention. Backcrossing in two or even three traits (for example the glyphosate, Europe corn borer, corn rootworm resistant genes) is routinely done with the use of marker assisted breeding techniques. This introduction of transgenes or mutations into a maize line is often called single gene conversion. Although, presently more than one gene particularly transgenes or mutations which are readily tracked with markers can be moved during the same "single gene conversion" process, resulting in a line with the addition of more targeted traits than just the one, but still having the characteristics of the present invention plus those characteristics added by the targeted traits.

The method of introducing a desired trait into maize inbred line comprising: (a) crossing plant grown from the present invention seed, representative seed of which has been deposited the recurrent parent, with plant of another maize line that comprises at least one target trait selected from the group consisting of nucleic acid encoding an enzyme selected from the group consisting of phytase, stearyl-ACP desaturase, fructosyltransferase, levansucrase, amylase, invertase and starch branching enzyme, the donor parent to produce F1 plants; (b) selecting for the targeted trait from the F1 plants, forming a pool of progeny plants; (c) crossing the progeny plants with the recurrent parent to produce backcrossed progeny plants; (d) selecting for backcrossed progeny plants that have at least one of the target trait and physiological and morphological characteristics of maize inbred line of the present invention a listed in Table 1 forming a pool of backcrossed progeny plants; and repeating a step of crossing the new pool with the recurrent parent and selecting for the targeted trait and the recurrent parents characteristics until the selected plant is essentially the recurrent parent with the targeted trait or targeted traits. This selection and crossing may take at least 4 backcrosses if marker assisted breeding is not employed.

The inbred line and seed of the present invention are employed to carry the agronomic package into the hybrid. Additionally, the inbred line is often carrying transgenes that are introduced in to the hybrid seed.

Likewise included is a first generation (F1) hybrid corn plant produced by the process of planting seeds of corn inbred line G06-NP2608; cultivating corn plants resulting from said planting; permitting pollen from inbred line G06-NP2608 to cross pollinate another inbred line; harvesting seeds produced on plants of the inbred; and growing a plant from such a harvested seed.

A number of different techniques exist which are designed to avoid detasseling in maize hybrid production. Some examples are switchable male sterility, lethal genes in the pollen or anther, inducible male sterility, male sterility genes with chemical restorers. There are numerous patented means of improving upon the hybrid production system. Some examples include U.S. Pat. No. 6,025,546, which relates to the use of tapetum-specific promoters and the barnase gene to produce male sterility; U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids and/or genes or traits to produce male sterility in maize inbreds or hybrids.

The inbred corn line G06-NP2608 and at least one transgenic gene adapted to give G06-NP2608 additional and/or altered phenotypic traits are within the scope of the invention. Such transgenes are usually associated with regulatory elements (promoters, enhancers, terminators and the like). Presently, transgenes provide the invention with traits such as insect resistance, herbicide resistance, disease resistance increased or deceased starch or sugars or oils, increased or decreased life cycle or other altered trait.

The present invention includes inbred corn line G06-NP2608 and at least one transgenic gene adapted to give G06-NP2608 modified starch traits. Furthermore this invention includes the inbred corn line G06-NP2608 and at least one mutant gene adapted to give modified starch, acid or oil traits, i.e. amylase, waxy, amylose extender or amylose. The present invention includes the inbred corn line G06-NP2608 and at least one transgenic gene: *bacillus thuringiensis*, the bar or pat gene encoding Phosphinothricin acetyl Transferase, Gdha gene, GOX, VIP, EPSP synthase gene, low phytic acid producing gene, and zein. The inbred corn line G06-NP2608 and at least one transgenic gene useful as a selectable marker or a screenable marker is covered by the present invention.

A tissue culture of the regenerable cells of hybrid plants produced with use of G06-NP2608 genetic material is covered by this invention. A tissue culture of the regenerable cells of the corn plant produced by the method described above is also included.

DEFINITIONS

In the description and examples, which follow, a number of terms are used. In order to provide a clear and consistent understanding of the specifications and claims, including the scope to be given such terms, the following definitions are provided.

Plant

This term includes the entire plant and its plant cells, plant protoplasts made from its cells, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like, and this term also includes any mutated gene, transgenic DNA or (RNA) or portion thereof that have been introduced into the plant by whatever method.

TWT

The measure of the weight of grain in pounds for a one bushel volume adjusted for percent grain moisture.

% Dropped Ears (DE) or PCTDE

The number of plants per plot, which dropped their primary ear, divided by the total number of plants per plot.

% Root Lodge (RL) or PCTRL

Percentage of plants per plot leaning more that 30 degrees from vertical divided by total plants per plot.

Yield (YLD)

Actual yield of grain at harvest adjusted to 15.5% moisture. Measurements are reported in bushels per acre.

Moisture

The average percentage grain moisture of an inbred or hybrid at harvest time.

% Stalk Lodge (SL) or PCTSL

Percentage of plants per plot with the stalk broken below the primary ear node divided by the total plants per plot.

GREEN SNAP (Gsnap): Count the number of plants in yield rows that snapped below the ear due to brittleness associated with high winds. For FET plots, count snapped plants out of 50 from two locations in each hybrid strip, sum, and record the percentage.

STAY-GREEN (Sgreen): This is an assessment of the ability of a grain hybrid to retain green color as maturity approaches (taken near the time of black-layer) and should not be a reflection of hybrid maturity or leaf disease. Record % of green tissue.

STAND: Shall mean the number of plants in the plot that were harvested.

| Color Choices: | | |
|---|---|---|
| 1. light green | 10. pink-orange | 19. white |
| 2. medium green | 11. pink | 20. white capped |
| 3. dark green | 12. light red | 21. buff |
| 4. very dark green | 13. cherry red | 22. tan |
| 5. green-yellow | 14. red | 23. brown |
| 6. pale yellow | 15. red and white | 24. bronze |
| 7. yellow | 16. pale purple (describe) | 25. variegated |
| 8. yellow-orange | 17. purple | 26. other (describe) |
| 9. salmon | 18. colorless | |

| Form # | ABR. | Description | Input Value |
|---|---|---|---|
| A1 | EMRGN | Final number of plants per plot | # |
| A2 | REGNN | Region Developed: 1. Northwest 2. Northcentral 3. Northeast 4. Southeast 5. Southcentral 6. Southwest 7. Other | # |
| A3 | CRTYN | Cross type: 1. sc 2. dc 3. 3w 4. msc 5. m3w 6. inbred 7. rel. line 8. other | # |
| A4 | KRTPN | Kernel type: 1. sweet 2. dent 3. flint 4. flour 5. pop 6. ornamental 7. pipecorn 8. other | # |
| A5 | EMERN | Days to Emergence EMERN | #Days |
| B1 | ERTLP | % Root lodging: (before anthesis): | #% |
| B2 | GRSNP | % Brittle snapping: (before anthesis): | #% |
| C1 | TBANN | Tassel branch angle of 2nd primary lateral branch (at anthesis): | degree |
| C10 | HUPSN | Heat units to 50% pollen shed: (from emergence) | #HU |
| C11 | SLKCN | Silk color: | #/Munsell value |
| C12 | HU5SN | Heat units to 50% silk: (from emergence) | #HU |
| C13 | DSAZN | Days to 50% silk in adapted zone: | #Days |
| C14 | HU9PN | Heat units to 90% pollen shed: (from emergence) | #HU |
| C15 | HU19N | Heat units from 10% to 90% pollen shed: | #HU |
| C16 | DA19N | Days from 10% to 90% pollen shed: | #Days |
| C2 | LSPUR | Leaf sheath pubescence of second leaf above the ear (at anthesis) 1-9 (1 = none): | # |
| C3 | ANGBN | Angle between stalk and 2nd leaf above the ear (at anthesis): | degree |
| C4 | CR2LN | Color of 2nd leaf above the ear (at anthesis): | #/Munsell value |
| C5 | GLCRN | Glume Color: | #/Munsell value |
| C6 | GLCBN | Glume color bars perpendicular to their veins (glume bands): 1. absent 2. present | # |
| C7 | ANTCN | Anther color: | #/Munsell value |
| C8 | PLQUR | Pollen Shed: 1-9 (0 = male sterile) | # |
| C9 | HU1PN | Heat units to 10% pollen shed: (from emergence) | #HU |
| D1 | LAERN | Number of leaves above the top ear node: | # |
| D10 | LTBRN | Number of lateral tassel branches that originate from the central spike: | # |
| D11 | EARPN | Number of ears per stalk: | # |
| D12 | APBRR | Anthocyanin pigment of brace roots: 1. absent 2. faint 3. moderate 4. dark | # |
| D13 | TILLN | Number of tillers: | # |
| D14 | HSKCN | Husk color 25 days after 50% silk: (fresh) | #/Munsell value |
| D2 | MLWVR | Leaf marginal waves: 1-9 (1 = none) | # |
| D3 | LFLCR | Leaf longitudinal creases: 1-9 (1 = none) | # |
| D4 | ERLLN | Length of ear leaf at the top ear node: | #cm |
| D5 | ERLWN | Width of ear leaf at the top ear node at the widest point: | #cm |
| D6 | PLHTN | Plant height to tassel tip: | #cm |
| D7 | ERHCN | Plant height to the top ear node: | #cm |
| D8 | LTEIN | Length of the internode between the ear node and the node above: | #cm |
| D9 | LTASN | Length of the tassel from top leaf collar to tassel tip: | #cm |
| E1 | HSKDN | Husk color 65 days after 50% silk: (dry) | #/Munsell value |
| E10 | DSGMN | Days from 50% silk to 25% grain moisture in adapted zone: | #Days |
| E11 | SHLNN | Shank length: | #cm |
| E12 | ERLNN | Ear length: | #cm |
| E13 | ERDIN | Diameter of the ear at the midpoint: | #mm |
| E14 | EWGTN | Weight of a husked ear: | #gm |
| E15 | KRRWR | Kernel rows: 1. indistinct 2. distinct | # |
| E16 | KRNAR | Kernel row alignment: 1. straight 2. slightly curved 3. curved | # |
| E17 | ETAPR | Ear taper: 1. slight 2. average 3. extreme | # |
| E18 | KRRWN | Number of kernel rows: | # |
| E19 | COBCN | Cob color: | #/Munsell value |
| E2 | HSKTR | Husk tightness 65 days after 50% silk: 1-9 (1 = loose) | # |
| E20 | COBDN | Diameter of the cob at the midpoint: | #mm |
| E21 | YBUAN | Yield: | #kg/ha |
| E22 | KRTEN | Endosperm type: 1. sweet 2. extra sweet 3. normal 4. high amylose 5. waxy 6. high protein 7. high lysine 8. super sweet 9. high oil 10. other | 3 |
| E23 | KRCLN | Hard endosperm color: | #/Munsell value |
| E24 | ALECN | Aleurone color: | #/Munsell value |
| E25 | ALCPR | Aleurone color pattern: 1. homozygous 2. segregating | # |
| E26 | KRLNN | Kernel length: | #mm |
| E27 | KRWDN | Kernel width: | #mm |
| E28 | KRDPN | Kernel thickness: | #mm |
| E29 | K1KHN | 100 kernel weight: | #gm |
| E3 | HSKCR | Husk extension: 1. short (ear exposed) 2. medium (8 cm) 3. long (8-10 cm) 4. very long (>10 cm) | # |
| E30 | KRPRN | % round kernels on 13/64 slotted screen: | #% |
| E4 | HEPSR | Position of ear 65 days after 50% silk: 1. upright 2. horizontal 3. pendent | # |
| E5 | STGRP | Staygreen 65 days after anthesis: 1-9 (1 = worst) | # |
| E6 | DPOPP | % dropped ears 65 days after anthesis: | % |
| E7 | LRTRP | % root lodging 65 days after anthesis: | % |
| E8 | HU25N | Heat units to 25% grain moisture: (from emergence) | #HU |
| E9 | HUSGN | Heat units from 50% silk to 25% grain moisture in adapted zone: | #HU |

DETAILED DESCRIPTION OF THE INVENTION

G06-NP2608 is shown in comparison with a number of standard inbreds used for comparison by the US PVP office. The present inbred is in the hybrid, X55864 and has a relative maturity of 5.5 and is a 105 day hybrid.

The inbred provides uniformity and stability within the limits of environmental influence for traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G06-NP2608.

The best method of producing the invention, G06-NP2608 which is substantially homozygous, is by planting the seed of G06-NP2608 which is substantially homozygous and self-pollinating or sib pollinating the resultant plant in an isolated environment, and harvesting the resultant seed.

This is a summary of some of the color traits listed in Table one below.

| | | | |
|---|---|---|---|
| SLKCN | Silk color: | 1 | light green |
| CR2LN | Color of 2nd leaf above the ear (at anthesis): | 4 | very dark green |
| GLCRN | Glume Color: | 1 | light green |
| GLCBN | Glume color bars perpendicular to their veins (glume bands): 1. absent 2. present | 2 | present |
| ANTCN | Anther color: | 13 | cherry red |
| APBRR | Anthocyanin pigment of brace roots: 1. absent 2. faint 3. moderate 4. dark | 3.5 | mod/dark |
| COBCN | Cob color: | 12.5 | light red/cherry red |
| KRCLN | Hard endosperm color: | 8 | yellow-orange |
| ALECN | Aleurone color: | 18 | colorless |

TABLE 1

G06-NP2608
VARIETY DESCRIPTION INFORMATION

| Trait | B37 | B64 | B68 | B73 | B76 | NP2598 | G06-NP2608 | NP2739 | NP2742 | NP2744 | NPFX8042 | NP2743 | H84 |
|---|---|---|---|---|---|---|---|---|---|---|---|---|---|
| YGSMN | 39.4 | 37.2 | 53.4 | 88.9 | 55.1 | 99.1 | 90.8 | 88.4 | 72.4 | 72.6 | 123.9 | 85.3 | 74.7 |
| LRTLP | 0.0 | 0.0 | 0.0 | 0.0 | 0.0 | 0.0 | 0.0 | 0.0 | 0.0 | 0.0 | 0.0 | 0.0 | 0.0 |
| ERTLP | 0.0 | 0.0 | 0.0 | 0.0 | 0.0 | 0.0 | 0.0 | 0.0 | 0.0 | 0.0 | 0.0 | 0.0 | 0.0 |
| NHL_P | 0.0 | 0.0 | 0.0 | 0.0 | 0.0 | 0.0 | 0.0 | 0.0 | 0.0 | 0.0 | 0.0 | 0.0 | 0.0 |
| EMRGN | 57.8 | 52.0 | 58.5 | 62.5 | 57.5 | 65.5 | 67.0 | 66.0 | 63.5 | 61.8 | 46.0 | 67.5 | 37.0 |
| STD_N | 57.8 | 52.0 | 58.5 | 62.5 | 57.5 | 65.5 | 67.0 | 66.0 | 63.5 | 61.8 | 46.0 | 67.5 | 37.0 |
| GRSNP | −0.1 | 0.0 | 0.0 | 0.0 | 0.0 | 0.0 | 0.0 | 0.0 | 0.0 | −0.1 | 0.0 | 0.0 | 0.0 |
| HSKCR | 2.0 | 2.5 | 3.0 | 3.0 | 1.5 | 2.0 | 2.0 | 2.0 | 3.0 | 2.0 | 2.5 | 2.0 | 2.0 |
| HU5SN | 776.5 | 1438.0 | 1527.0 | 1341.0 | 1332.5 | 1355.0 | 1277.5 | 1352.0 | 1341.0 | 631.0 | 1280.0 | 1341.0 | 1401.5 |
| PLHTN | 225.8 | 236.9 | 219.8 | 227.9 | 191.4 | 198.8 | 208.5 | 234.4 | 210.1 | 225.8 | 223.3 | 209.2 | 195.2 |
| ERHTN | 95.6 | 106.6 | 84.0 | 91.8 | 80.1 | 77.7 | 75.1 | 93.3 | 76.9 | 79.8 | 86.8 | 79.1 | 64.3 |
| HU1PN | 670.5 | 1364.5 | 1355.0 | 1241.0 | 1279.0 | 1301.5 | 1213.5 | 1338.0 | 1303.0 | 594.5 | 1271.0 | 1287.5 | 1242.0 |
| HU9PN | 723.5 | 1491.0 | 1447.0 | 1341.0 | 1371.5 | 1429.0 | 1289.5 | 1412.5 | 1369.0 | 643.0 | 1369.0 | 1355.0 | 1342.0 |
| HUPSN | 693.5 | 1424.5 | 1405.5 | 1315.0 | 1323.5 | 1341.0 | 1241.0 | 1366.0 | 1327.0 | 605.5 | 1312.5 | 1327.0 | 1295.5 |
| PLQUR | 7.0 | 6.0 | 7.0 | 7.5 | 6.5 | 5.5 | 6.5 | 8.0 | 5.5 | 4.0 | 7.5 | 6.0 | 6.5 |
| EARPN | 1.2 | 1.5 | 1.2 | 1.0 | 1.0 | 1.4 | 2.2 | 1.5 | 1.1 | 2.4 | 1.5 | 1.1 | 1.4 |
| SHLNN | 9.0 | 10.8 | 12.8 | 8.3 | 8.0 | 7.5 | 8.0 | 5.5 | 6.3 | 10.5 | 6.0 | 5.3 | 14.8 |
| ALCPR | 1.0 | 1.0 | 1.0 | 1.0 | 1.0 | 1.0 | 1.0 | 1.0 | 1.0 | 1.0 | 1.0 | 1.0 | 1.0 |
| ALECN | 18.0 | 18.0 | 18.0 | 18.0 | 18.0 | 18.0 | 18.0 | 18.0 | 18.0 | 18.0 | 18.0 | 18.0 | 18.0 |
| ANTCN | 14.0 | 3.5 | 5.5 | 6.5 | 14.0 | 5.5 | 13.0 | 11.5 | 12.0 | 11.0 | 6.0 | 6.0 | 13.0 |
| COBCN | 11.0 | 19.0 | 13.5 | 14.0 | 11.0 | 14.0 | 12.5 | 16.0 | 11.0 | 14.0 | 19.0 | 19.0 | 14.0 |
| CR2LN | 4.0 | 4.0 | 4.0 | 4.0 | 4.0 | 4.0 | 4.0 | 4.0 | 4.0 | 4.0 | 3.5 | 4.0 | 4.0 |

TABLE 1-continued

G06-NP2608
VARIETY DESCRIPTION INFORMATION

| | | | | | | | | | | | | | |
|---|---|---|---|---|---|---|---|---|---|---|---|---|---|
| CRTYN | 6.0 | 6.0 | 6.0 | 6.0 | 6.0 | 6.0 | 6.0 | 6.0 | 6.0 | 6.0 | 6.0 | 6.0 | 6.0 |
| DA19N | 2.5 | 5.5 | 4.5 | 4.0 | 4.0 | 5.5 | 3.5 | 3.0 | 2.5 | 2.0 | 4.5 | 2.5 | 4.0 |
| DSAZN | 32.5 | 60.5 | 64.0 | 56.0 | 56.0 | 56.5 | 53.5 | 56.5 | 56.0 | 26.5 | 53.0 | 56.0 | 59.0 |
| DSGMN | 47.0 | 51.0 | 49.0 | 53.0 | 54.5 | 56.0 | 59.5 | 55.5 | 58.5 | 54.0 | 51.5 | 53.0 | 54.0 |
| GLCBN | 1.0 | 2.0 | 1.0 | 1.0 | 1.0 | 1.0 | 2.0 | 1.0 | 1.0 | 1.0 | 1.0 | 1.0 | 1.0 |
| GLCRN | 2.0 | 2.5 | 1.5 | 2.0 | 2.0 | 2.5 | 3.0 | 2.5 | 2.5 | 2.0 | 2.5 | 2.0 | 3.0 |
| HSKCN | 2.0 | 2.5 | 2.0 | 2.0 | 2.0 | 2.0 | 3.0 | 2.0 | 2.5 | 2.0 | 2.0 | 2.5 | 3.0 |
| HSKDN | 21.0 | 21.0 | 21.0 | 21.0 | 21.0 | 21.0 | 21.0 | 21.0 | 21.0 | 21.0 | 21.0 | 21.0 | 21.0 |
| HU19N | 53.0 | 126.5 | 92.0 | 100.0 | 92.5 | 127.5 | 76.0 | 74.5 | 66.0 | 48.5 | 98.0 | 67.5 | 100.0 |
| HU25N | 2545.0 | 2522.5 | 2554.0 | 2489.5 | 2501.0 | 2553.5 | 2559.0 | 2522.0 | 2587.5 | 2436.0 | 2396.0 | 2488.0 | 2557.5 |
| HUSGN | 992.0 | 1084.5 | 1027.0 | 1148.5 | 1168.5 | 1198.5 | 1281.5 | 1200.0 | 1246.5 | 1174.0 | 1116.0 | 1147.0 | 1156.0 |
| KRCLN | 8.0 | 8.0 | 8.0 | 8.0 | 8.0 | 8.0 | 8.0 | 7.5 | 8.0 | 8.0 | 8.0 | 8.0 | 8.0 |
| KRTEN | 3.0 | 3.0 | 3.0 | 3.0 | 3.0 | 3.0 | 3.0 | 3.0 | 3.0 | 3.0 | 3.0 | 3.0 | 3.0 |
| KRTPN | 2.0 | 2.0 | 2.0 | 2.0 | 2.0 | 2.0 | 2.0 | 2.0 | 2.0 | 2.0 | 2.0 | 2.0 | 2.0 |
| SLKCN | 5.0 | 13.0 | 1.0 | 3.0 | 3.0 | 5.0 | 1.0 | 1.0 | 3.0 | 1.0 | 1.0 | 1.0 | 1.0 |
| LTEIN | 14.0 | 14.0 | 14.5 | 17.0 | 13.0 | 12.0 | 14.5 | 13.5 | 15.5 | 15.0 | 13.0 | 13.5 | 12.0 |
| ERLWN | 7.8 | 7.9 | 7.7 | 8.2 | 9.6 | 8.7 | 8.4 | 8.3 | 7.2 | 7.6 | 9.6 | 7.5 | 7.9 |
| ERLLN | 72.8 | 92.0 | 91.5 | 75.3 | 67.4 | 76.6 | 78.1 | 71.8 | 75.4 | 72.0 | 86.4 | 65.8 | 72.7 |
| LAERN | 6.6 | 6.3 | 6.9 | 6.0 | 5.7 | 6.6 | 6.1 | 7.2 | 5.1 | 6.4 | 6.0 | 5.5 | 7.6 |
| ANGBN | 20.0 | 27.5 | 40.0 | 20.0 | 25.0 | 27.5 | 25.0 | 32.5 | 15.0 | 15.0 | 22.5 | 22.5 | 27.5 |
| LTBRN | 8.8 | 7.9 | 8.1 | 6.6 | 6.2 | 7.7 | 1.9 | 2.5 | 5.2 | 3.6 | 8.2 | 4.4 | 5.1 |
| TBANN | 35.0 | 45.0 | 37.5 | 15.0 | 40.0 | 27.5 | 30.0 | 17.5 | 32.5 | 15.0 | 20.0 | 37.5 | 37.5 |
| LTASN | 37.7 | 46.8 | 38.1 | 40.6 | 37.5 | 42.3 | 34.1 | 38.2 | 40.1 | 44.8 | 47.4 | 33.1 | 31.8 |
| ERLNN | 14.5 | 18.1 | 17.4 | 14.6 | 13.5 | 16.2 | 14.2 | 15.9 | 14.4 | 16.0 | 16.4 | 14.5 | 14.2 |
| ERDIN | 36.4 | 36.0 | 38.3 | 44.7 | 40.1 | 42.6 | 39.7 | 38.3 | 40.0 | 36.2 | 44.7 | 40.9 | 41.2 |
| EWGTN | 62.4 | 66.3 | 76.4 | 112.8 | 72.8 | 119.2 | 109.7 | 105.9 | 89.9 | 90.6 | 149.7 | 99.2 | 98.6 |
| KRRWN | 12.0 | 13.0 | 15.2 | 17.6 | 13.2 | 16.0 | 15.4 | 13.6 | 13.4 | 13.6 | 16.2 | 14.6 | 14.8 |
| KRLNN | 8.5 | 9.0 | 10.0 | 10.8 | 10.8 | 10.8 | 10.5 | 11.0 | 10.3 | 10.0 | 11.8 | 11.5 | 11.5 |
| KRWDN | 8.0 | 7.5 | 7.0 | 7.3 | 9.5 | 6.8 | 7.5 | 8.3 | 8.3 | 6.5 | 7.8 | 7.5 | 8.3 |
| KRDPN | 5.5 | 5.0 | 4.8 | 5.0 | 5.5 | 4.3 | 4.0 | 4.3 | 5.3 | 3.5 | 4.5 | 4.3 | 5.3 |
| KRPRN | 97.0 | 81.0 | 61.0 | 40.0 | 84.0 | 27.5 | 60.5 | 35.0 | 74.5 | 89.0 | 35.0 | 22.0 | 57.0 |
| COBDN | 22.7 | 24.2 | 25.5 | 27.8 | 26.0 | 25.7 | 23.0 | 22.2 | 24.6 | 21.5 | 27.7 | 21.8 | 24.3 |
| APBRR | 2.0 | 3.0 | 4.0 | 3.5 | 2.5 | 2.0 | 3.5 | 2.0 | 3.0 | 2.0 | 2.0 | 2.5 | 2.0 |
| LSPUR | 1.0 | 7.0 | 7.5 | 5.0 | 3.5 | 4.5 | 6.0 | 2.0 | 2.5 | 3.0 | 7.5 | 3.0 | 2.0 |
| MLWVR | 8.0 | 6.0 | 4.5 | 5.0 | 6.5 | 3.0 | 4.0 | 4.0 | 4.5 | 5.0 | 3.5 | 4.5 | 7.0 |
| LFLCR | 3.0 | 3.0 | 4.0 | 3.5 | 4.5 | 4.5 | 2.5 | 4.0 | 3.5 | 4.0 | 2.5 | 2.5 | 2.5 |

TABLE 1-continued

G06-NP2608
VARIETY DESCRIPTION INFORMATION

| | | | | | | | | | | | | | |
|---|---|---|---|---|---|---|---|---|---|---|---|---|---|
| HSKTR | 7.0 | 7.5 | 6.5 | 6.5 | 3.0 | 7.5 | 5.5 | 5.0 | 5.5 | 6.0 | 7.0 | 6.0 | 4.5 |
| HEPSR | 1.0 | 1.0 | 1.0 | 2.0 | 1.0 | 1.0 | 1.0 | 3.0 | 1.0 | 1.0 | 1.5 | 2.5 | 1.0 |
| KRRWR | 1.0 | 1.5 | 2.0 | 2.0 | 2.0 | 2.0 | 2.0 | 2.0 | 2.0 | 2.0 | 2.0 | 2.0 | 2.0 |
| ETAPR | 2.0 | 2.0 | 2.0 | 1.5 | 1.0 | 1.0 | 2.0 | 1.0 | 1.0 | 1.0 | 2.0 | 1.0 | 1.0 |
| K1KHN | 29.0 | 29.5 | 24.0 | 25.5 | 30.0 | 26.0 | 28.0 | 28.5 | 31.5 | 33.0 | 28.5 | 25.0 | 29.0 |
| TILLN | 0.0 | 0.0 | 0.0 | 0.0 | 0.0 | 0.0 | 0.0 | 0.0 | 0.0 | 0.0 | 0.0 | 0.0 | 0.0 |
| TILLP | 0.0 | 0.0 | 0.0 | 0.0 | 0.0 | 0.0 | 0.0 | 0.0 | 0.0 | 0.0 | 0.0 | 0.0 | 0.0 |
| DROPP | 0.0 | 0.0 | 0.0 | 0.0 | 0.0 | 0.0 | 0.0 | 0.0 | 0.0 | 0.0 | 0.0 | 2.2 | 0.0 |
| KERAR | 3.0 | 2.0 | 1.0 | 1.0 | 1.5 | 1.5 | 1.5 | 1.5 | 2.0 | 2.0 | 2.0 | 2.0 | 2.0 |

| Trait | H89 | MS71 | Mo17 | N192 | NC268 | Pa91 | Va26 | Va35 | W64a |
|---|---|---|---|---|---|---|---|---|---|
| YGSMN | 47.3 | 54.9 | 87.0 | 62.2 | 50.3 | 78.9 | 76.0 | 100.3 | 70.6 |
| LRTLP | 0.0 | 0.0 | 0.0 | 0.0 | 0.0 | 0.0 | 0.0 | 0.0 | 0.0 |
| ERTLP | 0.0 | 0.0 | 0.0 | 0.0 | 0.0 | 0.0 | 0.0 | 0.0 | 0.0 |
| NHL_P | 0.0 | 0.0 | 0.0 | 0.0 | 0.0 | 0.0 | 0.0 | 0.0 | 0.0 |
| EMRGN | 56.5 | 54.8 | 63.0 | 63.0 | 59.5 | 51.2 | 55.2 | 62.5 | 64.5 |
| STD_N | 56.5 | 54.8 | 63.0 | 63.0 | 59.5 | 51.2 | 55.2 | 62.5 | 64.5 |
| GRSNP | 0.0 | −0.1 | 0.0 | 0.0 | 0.0 | 0.1 | 0.1 | 0.0 | 0.0 |
| HSKCR | 2.0 | 2.0 | 2.0 | 2.0 | 3.0 | 2.0 | 2.0 | 1.0 | 2.0 |
| HU5SN | 1289.0 | 693.5 | 1415.0 | 1329.5 | 1487.0 | 731.5 | 710.0 | 1383.0 | 1216.0 |
| PLHTN | 143.8 | 164.0 | 231.7 | 198.8 | 199.2 | 234.2 | 251.2 | 209.5 | 182.4 |
| ERHTN | 35.8 | 60.0 | 97.3 | 75.7 | 80.3 | 92.6 | 92.2 | 79.8 | 73.6 |
| HU1PN | 1177.0 | 631.0 | 1250.0 | 1185.0 | 1422.0 | 671.0 | 617.5 | 1313.5 | 1127.5 |
| HU9PN | 1327.0 | 693.5 | 1350.0 | 1280.5 | 1547.0 | 718.0 | 698.5 | 1392.0 | 1217.5 |
| HUPSN | 1250.0 | 656.5 | 1301.0 | 1227.5 | 1473.5 | 691.5 | 671.0 | 1364.5 | 1171.0 |
| PLQUR | 6.5 | 9.0 | 4.5 | 6.5 | 5.0 | 7.0 | 9.0 | 5.5 | 8.0 |
| EARPN | 1.2 | 1.2 | 1.4 | 1.0 | 1.5 | 1.4 | 1.0 | 1.0 | 1.0 |
| SHLNN | 5.5 | 8.0 | 12.3 | 9.3 | 5.8 | 7.0 | 7.5 | 6.8 | 6.5 |
| ALCPR | 1.0 | 1.0 | 1.0 | 1.0 | 1.0 | 1.0 | 1.0 | 1.0 | 1.0 |
| ALECN | 18.0 | 18.0 | 18.0 | 18.0 | 18.0 | 18.0 | 18.0 | 18.0 | 18.0 |
| ANTCN | 5.0 | 5.0 | 5.0 | 6.0 | 8.5 | 5.0 | 5.0 | 5.0 | 5.0 |
| COBCN | 19.0 | 14.0 | 12.5 | 10.0 | 12.5 | 9.0 | 19.0 | 13.5 | 14.0 |
| CR2LN | 4.0 | 3.0 | 4.0 | 4.0 | 4.0 | 4.0 | 4.0 | 4.0 | 3.5 |
| CRTYN | 6.0 | 6.0 | 6.0 | 6.0 | 6.0 | 6.0 | 6.0 | 6.0 | 6.0 |
| DA19N | 7.0 | 2.5 | 4.0 | 5.0 | 5.0 | 2.0 | 3.5 | 4.0 | 4.5 |
| DSAZN | 54.0 | 29.0 | 59.5 | 55.5 | 62.5 | 30.5 | 30.0 | 58.0 | 51.0 |
| DSGMN | 50.0 | 43.0 | 46.5 | 49.0 | 55.0 | 58.0 | 43.0 | 53.5 | 52.0 |
| GLCBN | 2.0 | 1.0 | 1.0 | 1.0 | 1.0 | 1.0 | 1.0 | 1.0 | 1.0 |
| GLCRN | 2.0 | 2.0 | 3.0 | 2.0 | 2.0 | 2.0 | 1.0 | 3.0 | 1.0 |
| HSKCN | 3.0 | 2.0 | 2.5 | 2.5 | 2.0 | 3.0 | 2.0 | 2.5 | 2.5 |
| HSKDN | 21.0 | 21.0 | 21.0 | 21.0 | 21.0 | 21.0 | 21.0 | 21.0 | 21.0 |
| HU19N | 150.0 | 62.5 | 100.0 | 95.5 | 125.0 | 47.0 | 81.0 | 78.5 | 90.0 |
| HU25N | 2387.0 | 2335.0 | 2433.0 | 2412.0 | 2636.5 | 2488.0 | 2360.0 | 2526.0 | 2368.0 |
| HUSGN | 1098.0 | 948.0 | 1018.0 | 1082.5 | 1149.5 | 1025.0 | 940.0 | 1143.0 | 1152.0 |
| KRCLN | 8.0 | 8.0 | 8.0 | 8.0 | 8.0 | 8.0 | | 8.0 | 8.0 |
| KRTEN | 3.0 | 3.0 | 3.0 | 3.0 | 3.0 | 3.0 | 3.0 | 3.0 | 3.0 |
| KRTPN | 2.0 | 2.0 | 2.0 | 2.0 | 2.0 | 2.0 | 2.0 | 2.0 | 2.0 |
| SLKCN | 3.0 | 5.0 | 3.0 | 3.0 | 3.0 | 5.0 | 5.0 | 3.0 | 1.0 |
| LTEIN | 11.0 | 11.0 | 15.0 | 11.0 | 10.5 | 14.0 | 14.0 | 13.0 | 12.0 |
| ERLWN | 7.3 | 6.4 | 8.7 | 8.7 | 8.6 | 9.4 | 9.2 | 9.0 | 8.6 |
| ERLLN | 61.2 | 71.5 | 72.2 | 78.3 | 71.8 | 93.4 | 79.2 | 72.3 | 66.9 |
| LAERN | 7.2 | 6.0 | 5.1 | 5.7 | 7.8 | 5.8 | 7.0 | 6.4 | 6.0 |
| ANGBN | 45.0 | 30.0 | 27.5 | 17.5 | 30.0 | 35.0 | 25.0 | 15.0 | 35.0 |
| LTBRN | 3.3 | 12.0 | 6.9 | 5.7 | 7.7 | 10.4 | 22.6 | 7.5 | 6.1 |
| TBANN | 40.0 | 30.0 | 35.0 | 30.0 | 42.5 | 50.0 | 50.0 | 17.5 | 20.0 |
| LTASN | 32.4 | 36.8 | 49.1 | 38.4 | 28.7 | 46.2 | 40.4 | 41.8 | 35.5 |
| ERLNN | 13.8 | 14.2 | 19.0 | 14.6 | 14.6 | 14.9 | 14.6 | 17.6 | 13.8 |
| ERDIN | 34.6 | 34.8 | 36.7 | 37.0 | 35.9 | 40.2 | 39.5 | 39.2 | 40.7 |
| EWGTN | 65.8 | 75.6 | 103.1 | 80.6 | 64.5 | 96.6 | 92.0 | 123.7 | 95.4 |
| KRRWN | 11.3 | 15.2 | 11.4 | 15.0 | 12.4 | 15.6 | 15.6 | 12.6 | 16.4 |
| KRLNN | 8.8 | 9.0 | 10.5 | 10.0 | 11.3 | 9.5 | 11.5 | 9.8 | 9.3 |
| KRWDN | 8.3 | 7.0 | 8.5 | 7.0 | 8.3 | 7.5 | 7.5 | 8.0 | 7.0 |
| KRDPN | 4.5 | 4.5 | 5.0 | 4.0 | 4.3 | 5.5 | 5.0 | 5.8 | 4.0 |
| KRPRN | 46.5 | 50.0 | 51.5 | 55.5 | 43.0 | 75.0 | 62.0 | 63.5 | 31.0 |
| COBDN | 22.2 | 22.9 | 19.9 | 24.2 | 21.1 | 25.3 | 25.1 | 23.5 | 26.9 |

TABLE 1-continued

G06-NP2608
VARIETY DESCRIPTION INFORMATION

| | | | | | | | | | |
|---|---|---|---|---|---|---|---|---|---|
| APBRR | 1.5 | 2.0 | 2.0 | 4.0 | 3.5 | 2.0 | 2.0 | 2.5 | 2.0 |
| LSPUR | 2.0 | 4.0 | 2.0 | 8.5 | 2.5 | 1.0 | 4.0 | 4.0 | 7.0 |
| MLWVR | 3.5 | 3.0 | 5.0 | 5.5 | 3.5 | 5.0 | 7.0 | 3.0 | 4.0 |
| LFLCR | 4.0 | 3.0 | 5.0 | 4.5 | 4.5 | 2.0 | 3.0 | 2.5 | 4.0 |
| HSKTR | 5.5 | 4.0 | 3.0 | 4.5 | 8.0 | 7.0 | 6.0 | 4.5 | 2.0 |
| HEPSR | 3.0 | 3.0 | 1.5 | 2.0 | 1.0 | 1.0 | 2.0 | 1.0 | 3.0 |
| KRRWR | 2.0 | 2.0 | 2.0 | 2.0 | 2.0 | 2.0 | 2.0 | 2.0 | 2.0 |
| ETAPR | 1.0 | 2.0 | 1.5 | 1.0 | 1.0 | 1.0 | 1.0 | 1.0 | 1.5 |
| K1KHN | 23.0 | 20.0 | 31.5 | 24.5 | 29.0 | 28.0 | 27.0 | 31.0 | 23.0 |
| TILLN | 0.0 | 0.0 | 0.0 | 1.5 | 0.0 | 0.0 | 0.0 | 0.0 | 0.0 |
| TILLP | 0.0 | 0.0 | 0.0 | 2.4 | 0.0 | 0.0 | 0.0 | 0.0 | 0.0 |
| DROPP | 3.6 | 0.0 | 0.8 | 0.0 | 0.0 | 0.0 | 0.0 | 0.0 | 3.2 |
| KERAR | 1.5 | 1.0 | 1.5 | 1.0 | 1.0 | 1.0 | 1.0 | 1.5 | 1.0 |

The yield of G06-NP2608 is the third highest yield shown in this data. The final number of plants per plot for the present invention is 65 which is the second highest number of plants shown by the data of these various inbreds. The present invention shows an average pollen shed rating of 6.5 when compared with the other inbreds. The rating scale of 9-1 is used for most rating data. In all instances 9 is the best rating and 1 is the lowest rating. Heat Units per day were calculated: HU=[Max-Temp (86)–Min Temp (50)]/2–50. An inbred's response to environment is often more pronounced than a hybrid.

The data provided above is often a color. The Munsell code is a reference book of color, which is known and used in the industry and by persons with ordinary skill in the art of plant breeding.

Hybrid Performance of G06-NP2608

Table 2 shows the inbred G06-NP2608 in hybrid combination in X55864 in comparison with other hybrid combinations, which have a common inbred with the hybrid containing G06-NP2608 or are adapted for the same region. When in this hybrid combination the present inbred G06-NP2608 carries less moisture than Hybrid 1 and 2 but more moisture than hybrids 3 and 4. The present invention in this hybrid is not carrying the yield that hybrids 1-3 are carrying. On the other hand XX55864 shows good agronomic performance with little tendency to root of stalk lodging. The test weight for the hybrid combination containing the present invention is heavier than all of the other hybrids except hybrid 4.

TABLE 2

PAIRED HYBRID COMPARISON DATA

| AbbrCode | Yld | Moist | TWT | PCTSL | PCTRL | PCTDE | Stand | Sgreen | Gsnap |
|---|---|---|---|---|---|---|---|---|---|
| Hybrid 1 | 213.0 | 18.7 | 54.8 | 0.0 | 0.0 | 0.0 | 62.7 | 36.3 | 1.5 |
| Hybrid 2 | 202.1 | 18.1 | 56.5 | 1.5 | 10.7 | 0.0 | 63.5 | 7.5 | 0.0 |
| Hybrid 3 | 198.0 | 17.3 | 56.4 | 0.2 | 0.4 | 0.0 | 63.8 | 17.5 | 1.5 |
| X55864 | 197.3 | 17.1 | 56.6 | 0.1 | 1.3 | 0.0 | 63.7 | 23.8 | 0.0 |
| Hybrid 4 | 193.3 | 17.1 | 56.8 | 1.1 | 11.2 | 0.0 | 63.4 | 11.3 | 0.0 |

This invention also is directed to methods for producing a corn plant by crossing a first parent corn plant with a second parent corn plant wherein the first or second parent corn plant is an inbred corn plant from the line G06-NP2608. Further, both first and second parent corn plants can come from the inbred corn line G06-NP2608 which produces a self of the inbred invention. The present invention can be employed in a variety of breeding methods which can be selected depending on the mode of reproduction, the trait, and the condition of the germplasm. Thus, any breeding methods using the inbred corn line G06-NP2608 are part of this invention: selfing, backcrosses, hybrid production, and crosses to populations, and haploid by such old and known methods of using stock six material that induces haploids and anther culturing and the like.

All plants and plant cells produced using inbred corn line G06-NP2608 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line G06-NP2608.

Additionally, this maize can, within the scope of the invention, contain: a mutant gene such as, but not limited to, the amylose, amylase, sugary 1 or shrunken 1 or waxy or AE or imazethapyr tolerant (IT or IR™) mutant gene; or transgenic genes such as but not limited to insect resistant genes such as Corn Rootworm gene, *Bacillus thuringiensis* (Cry genes), or herbicide resistant genes such as Pat gene or Bar gene, EPSP, or disease resistant genes such as the Mosaic virus resistant gene, etc., or trait altering genes such as flowering genes, oil modifying genes, senescence genes and the like. The methods and techniques for inserting, or producing and/or identifying a mutation or a transgene into the present invention through breeding, transformation, or mutating are well known and understood by those of ordinary skill in the art.

A number of different inventions exist which are designed to avoid detasseling in maize hybrid production. Some examples are switchable male sterility, lethal genes in the pollen or anther, inducible male sterility, male sterility genes with chemical restorers, sterility genes linked with parent.

U.S. Pat. No. 6,025,546, relates to the use of tapetum-specific promoters and the barnase gene. U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids.

Various techniques for breeding and moving or altering genetic material within or into the present invention (whether it is an inbred or in hybrid combination) are also known to those skilled in the art. These techniques to list only a few are anther culturing, haploid production, (stock six is a method that has been in use for thirty years and is well known to those with skill in the art), transformation, irradiation to produce mutations, chemical or biological mutation agents and a host of other methods are within the scope of the invention. All parts of the G06-NP2608 plant including its plant cells produced using the inbred corn line is within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices. The transgene once introduced into plant material and integrated stably can be moved into other germplasm by standard breeding practices.

Though there are a large number of known methods to transform plants, certain types of plants are more amenable to transformation than are others. Transformation of dicots is usually achievable for example, tobacco is a readily transformable plant. Monocots can present some transformation challenges, however, the basic steps of transforming plants monocots have been known in the art for about 15 years. The most common method of maize transformation is referred to as gunning or microprojectile bombardment though other methods can be used. The process employs small gold-coated particles coated with DNA which are shot into the transformable material. Detailed techniques for gunning DNA into cells, tissue, callus, embryos, and the like are well known in the prior art. One example of steps that can be involved in monocot transformation are concisely outlined in U.S. Pat. No. 5,484,956 "Fertile Transgenic *Zea mays* Plants Comprising Heterologous DNA Encoding *Bacillus Thuringiensis* Endotoxin" issued Jan. 16, 1996 and also in U.S. Pat. No. 5,489,520 "Process of Producing Fertile *Zea mays* Plants and Progeny Comprising a Gene Encoding Phosphinothricin Acetyl Transferase" issued Feb. 6, 1996.

Plant cells such as maize can be transformed not only by the use of a gunning device but also by a number of different techniques. Some of these techniques include maize pollen transformation (See University of Toledo 1993 U.S. Pat. No. 5,177,010); Whiskers technology (See U.S. Pat. Nos. 5,464,765 and 5,302,523); electroporation; PEG on Maize; *Agrobacterium* (See 1996 article on transformation of maize cells in *Nature Biotechnology*, Volume 14, June 1996) along with numerous other methods which may have slightly lower efficiency rates. Some of these methods require specific types of cells and other methods can be practiced on any number of cell types.

The use of pollen, cotyledons, zygotic embryos, meristems and ovum as the target issue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming plant material is that it can form a transformed plant.

The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used. The transgenic gene can come from various non-plant genes (such as; bacteria, yeast, animals, and viruses) along with being from plants.

The regulatory promoters employed can be constitutive such as CaMv35S (usually for dicots) and polyubiquitin for monocots or tissue specific promoters such as CAB promoters, MR7 described in U.S. Pat. No. 5,837,848, etc. The prior art promoters, includes but is not limited to, octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular maize material are well known in the art.

A deposit of at least 2500 seeds of this invention will be maintained by Syngenta Seed Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The date of deposit was Feb. 8, 2008. The ATCC number of the deposit is PTA-8935 and on Feb. 29, 2008 the seeds were tested and found to be viable. The deposit of at least 2500 seeds will be from inbred seed taken from the deposit maintained by Syngenta Seed Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on patent variety protection may be available from the PVP Office, a division of the US Government.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

What is claimed is:

1. Seed of maize inbred line designated G06-NP2608, representative seed of said line having been deposited under ATCC Accession No. PTA-8935.

2. A maize plant, or a part thereof, produced by growing the seed of claim 1.

3. The maize plant of claim 2 wherein said plant has been detasseled.

4. A tissue culture of regenerable cells produced from the plant of claim 2.

5. Protoplasts produced from the tissue culture of claim 4.

6. The tissue culture of claim 4, wherein cells of the tissue culture are from a tissue selected from the group consisting of leaf, pollen, embryo, root, root tip, anther, silk, flower, kernel, ear, cob, husk and stalk.

7. A maize plant regenerated from the tissue culture of claim 4, said plant having all the morphological and physiological characteristics of inbred line G06-NP2608, representative seed of said line having been deposited under ATCC Accession No. PTA-8935.

8. A method for producing an F1 hybrid maize seed, comprising crossing the plant of claim 2 with a different maize plant and harvesting the resultant F1 hybrid maize seed.

9. A method of producing a male sterile maize plant comprising transforming the maize plant of claim 2 with a nucleic acid molecule that confers male sterility.

10. A male sterile maize plant produced by the method of claim 9.

11. A method of producing an herbicide resistant maize plant comprising transforming the maize plant of claim 2 with a transgene that confers herbicide resistance.

12. An herbicide resistant maize plant produced by the method of claim 11.

13. The maize plant of claim 12, wherein the transgene confers resistance to an herbicide selected from the group consisting of: imidazolinone, sulfonylurea, glyphosate, glufosinate, L-phosphinothricin, triazine and benzonitrile.

14. A method of producing an insect resistant maize plant comprising transforming the maize plant of claim 2 with a transgene that confers insect resistance.

15. An insect resistant maize plant produced by the method of claim 14.

16. The maize plant of claim 15, wherein the transgene encodes a *Bacillus thuringiensis* endotoxin.

17. A method of producing a disease resistant maize plant comprising transforming the maize plant of claim 2 with a transgene that confers disease resistance.

18. A disease resistant maize plant produced by the method of claim 17.

19. A method of producing a maize plant with decreased phytate content comprising transforming the maize plant of claim 2 with a transgene encoding phytase.

20. A maize plant with decreased phytate content produced by the method of claim 19.

21. A method of producing a maize plant with modified fatty acid metabolism or modified carbohydrate metabolism comprising transforming the maize plant of claim 2 with a transgene encoding a protein selected from the group consisting of stearyl-ACP desaturase, fructosyltransferase, levansucrase, alpha-amylase, invertase and starch branching enzyme.

22. A maize plant produced by the method of claim 21.

23. The maize plant of claim 22 wherein the transgene confers a trait selected from the group consisting of waxy starch and increased amylose starch.

24. A maize plant, or part thereof, having all the physiological and morphological characteristics of the inbred line G06-NP2608, representative seed of said line having been deposited under ATCC Accession No. PTA-8935.

25. A method of introducing a desired trait into maize inbred line G06-NP2608 comprising:
    (a) crossing G06-NP2608 plants grown from G06-NP2608 seed, representative seed of which has been deposited under ATCC Accession No. PTA-8935, with plants of another maize line that comprise a desired trait to produce F1 progeny plants, wherein the desired trait is selected from the group consisting of male sterility, herbicide resistance, insect resistance, disease resistance and waxy starch;
    (b) selecting F1 progeny plants that have the desired trait to produce selected F1 progeny plants;
    (c) crossing the selected progeny plants with the G06-NP2608 plants to produce backcross progeny plants;
    (d) selecting for backcross progeny plants that have the desired trait and physiological and morphological characteristics of maize inbred line G06-NP2608 listed in Table 1 to produce selected backcross progeny plants; and
    (e) repeating steps (c) and (d) three or more times in succession to produce selected fourth or higher backcross progeny plants that comprise the desired trait and all of the physiological and morphological characteristics of maize inbred line G06-NP2608 listed in Table 1 as determined at the 5% significance level when grown in the same environmental conditions.

26. A plant produced by the method of claim 25, wherein the plant has the desired trait and all of the physiological and morphological characteristics of maize inbred line G06-NP2608 listed in Table 1 as determined at the 5% significance level when grown in the same environmental conditions.

27. The plant of claim 26 wherein the desired trait is herbicide resistance and the resistance is conferred to an herbicide selected from the group consisting of: imidazolinone, sulfonylurea, glyphosate, glufosinate, L-phosphinothricin, triazine and benzonitrile.

28. The plant of claim 26 wherein the desired trait is insect resistance and the insect resistance is conferred by a transgene encoding a *Bacillus thuringiensis* endotoxin.

29. The plant of claim 26 wherein the desired trait is male sterility and the trait is conferred by a cytoplasmic nucleic acid molecule that confers male sterility.

30. A method of modifying fatty acid metabolism, modified phytic acid metabolism or modified carbohydrate metabolism into maize inbred line G06-NP2608 comprising:
    (a) crossing G06-NP2608 plants grown from G06-NP2608 seed, representative seed of which has been deposited under ATCC Accession No. PTA-8935, with plants of another maize line that comprise a nucleic acid molecule encoding an enzyme selected from the group consisting of phytase, stearyl-ACP desaturase, fructosyltransferase, levansucrase, alphaamylase, invertase and starch branching enzyme;

(b) selecting F1 progeny plants that have said nucleic acid molecule to produce selected F1 progeny plants;
(c) crossing the selected progeny plants with the G06-NP2608 plants to produce backcross progeny plants;
(d) selecting for backcross progeny plants that have said nucleic acid molecule and physiological and morphological characteristics of maize inbred line G06-NP2608 listed in Table 1 to produce selected backcross progeny plants; and
(e) repeating steps (c) and (d) three or more times in succession to produce selected fourth or higher backcross progeny plants that comprise said nucleic acid molecule and have all of the physiological and morphological characteristics of maize inbred line G06-NP2608 listed in Table 1 as determined at the 5% significance level when grown in the same environmental conditions.

31. A plant produced by the method of claim 30, wherein the plant comprises the nucleic acid molecule and has all of the physiological and morphological characteristics of maize inbred line G06-NP2608 listed in Table 1 as determined at the 5% significance level when grown in the same environmental conditions.

* * * * *